United States Patent [19]

Carlson

[11] 4,103,026

[45] Jul. 25, 1978

[54] TREATMENT OF PERIPHERAL VASCULAR DISEASE BY NON-INTRAARTERIAL ADMINISTRATION OF PROSTAGLANDIN $E_1$

[76] Inventor: Lars A. Carlson, Stora Malmgatan 19 S-190 30, Sigtuna, Sweden

[21] Appl. No.: 786,175

[22] Filed: Apr. 11, 1977

Related U.S. Application Data

[63] Continuation-in-part of Ser. No. 716,737, Aug. 23, 1976, abandoned.

[51] Int. Cl.² .................. A61K 31/215; A61K 31/19
[52] U.S. Cl. ..................................... 424/305; 424/317
[58] Field of Search ............................... 424/305, 317

[56] References Cited

PUBLICATIONS

Pike et al.–Prostaglandin Bibliography, Nov. 6, 1969 (Upjohn Co.) pp. 40, 58, 59 & 96.
Bevegard et al.–Scand. J. Clin. Lab. Invest., vol. 23 (1969), pp. 347–353.

*Primary Examiner*—Sam Rosen
*Attorney, Agent, or Firm*—Robert A. Armitage

[57] ABSTRACT

A method of treating peripheral vascular disease in humans by non-arterial, systemic administration of prostaglandin $E_1$, its pharmacologically acceptable salts, lower alkyl esters or amide.

14 Claims, No Drawings

TREATMENT OF PERIPHERAL VASCULAR DISEASE BY NON-INTRAARTERIAL ADMINISTRATION OF PROSTAGLANDIN $E_1$

CROSS REFERENCE TO RELATED APPLICATION

This application is a continuation-in-part of Ser. No. 716,737, filed Aug. 23, 1976, now abandoned.

BACKGROUND OF THE INVENTION $PGE_1$ is a naturally occurring prostaglandin. Further, various salts and lower alkyl esters of $PGE_1$ are known in the art. See, for example, U.S. Pat. No. 3,069,322. Likewise $PGE_1$ amide is described at Derwent Farmdoc CPI 32921W, abstracting French Published Application No. 2,239,458.

$PGE_1$, its lower alkyl esters, salts, and amide are known to be potent pharmacological agents. In particular, $PGE_1$ is known to be a potent vasodilator.

However, prostaglandins, including $PGE_1$, are known to be readily, metabolically inactivated, particularly during pulmonary circulation. Ferreira and Vane (Nature 216, 868, 1967) found that the biological activity of prostaglandin $E_1$ and $E_2$, although stable in blood, almost completely disappeared in a single pass through the pulmonary circulation of dogs, cats, and rabbits. Biron (Clin. Res. 16, 112, 1968) confirmed that over 80 percent of prostaglandins perfused through the lung were extracted in rabbits, rats, cats, and dogs. McGiff et al., (Nature 223, 742, 1969) found that $PGE_1$ was removed by the lung exceedingly rapidly and concluded that its activities were restricted essentially to the area between the site of introduction into a vein and the site of pulmonary circulation where prostaglandins are inactivated. Horton and Jones (Brit. J. Pharmacol. 37, 705, 1969), cited the work of Ferreira and Vane (above) which showed that more than 95 percent of the smooth muscle stimulating activity of prostaglandin $E_2$ in the cat and more than 95 percent of the smooth muscle stimulating activity of $PGE_1$ in the dog were lost on a single passage through the lung, and obtained losses of peripheral vasodilator activity of prostaglandin $E_1$ on passage through the lung and liver circulation of the cat and dog which agreed closely with those noted above. Piper, Vane, and Wyllie (Nature 225, 600, 1970) and Piper and Vane (in Prostaglandins, Peptides, and Amines, ed. Mantegazza and Horton, 15, Academic Press, London, 1969) confirmed these findings and concluded that prostaglandin $E_1$, $E_2$, and $F_2\alpha$ are almost completely inactivated by the pulmonary circulation of the cat, dog, rat, and guinea pig. They further established that these prostaglandins were inactivated at all concentrations studied and concluded that an excess of pulmonary enzyme was available which metabolized essentially 100 percent of the PGE reaching the lung. Similarly Samuelsson (Ann. N.Y. Acad. Sci. 180, 138, 1971), injecting tritium labelled PGE into a vein of one arm and removing blood from the other arm found at least 90 percent of the injected prostaglandin had been metabolized during transit through the human lung in 1.5 min. In double-labelled studies, they were able to show that the human lung removed 97 percent of $PGE_2$ in 90 seconds and 99.5-100 percent in 4.5 min. (Hamberg and Samuelsson, J. Biol. Chem. 246, 6713, 1971). Using $PGF_2\alpha$ as a substrate, Granstrom (Eur. J. Biochem. 27, 462, 1971) found 97 percent to be removed in 90 seconds and 99.5 percent in 3.5 min. These investigations establish that the prostaglandin E's are converted to 15-keto metabolites within seconds after reaching the lung and that the metabolites are relative inactive.

Thus, heretofore the administration of $PGE_1$ in the treatment of human peripheral vascular disease was known only by administration of the prostaglandin into an artery leading to one or more affected extremities. Accordingly, this intraarterial administration would allow $PGE_1$ to exert its therapeutic effect at the site of the diseased vascular beds without first passing through the lung, and thus before being subjected to prostaglandin 15-dehydrogenase, prostaglandin 13-reductase or other known prostaglandin-inactivating enzymes of the lung.

However, intraarterial administration as taught in the prior art, represents an especially inconvenient and substantially more traumatic route of adminstration than other more routinely and conventionally employed parenteral routes (e.g., intravenous). Thus, intraarterial administration requires the continuous supervision by highly skilled medical professionals.

For a complete discussion of the nature of and clinical manifestations of human peripheral vascular disease and the method previously known of its intraarterial treatment with prostaglandins, see South African Patent 74/0149.

Further, the parenteral use of $PGE_1$ as a pharmacological agent, both for therapeutic and prophylactic purposes, is known in the art. For example, in addition to South African Patent No. 74/0149, numerous references describe the use of intravenous and intraarterial prostaglandins, including $PGE_1$, for maintaining the patency of the ductus arteriosus in newborn infants suffering from the "blue baby" syndrome. See R. B. Elliott, et al., Lancet, Jan. 18, 1975, pp. 140–142; P. M. Olley, et al., Circulation, 53:728 (1976); and F. Coceani, et al., Can. J. Physiol. Pharmacol 51:220 (1973).

SUMMARY OF THE INVENTION

The present invention relates to the surprising and unexpected efficacy of $PGE_1$ in the treatment of human peripheral vascular disease by non-arterial, systemic administration.

Accordingly, in a method of treating peripheral vascular diseases in the extremities of humans who have circulatory insufficiencies in said extremities; which consists essentially of systemic administration to said humans of $PGE_1$ in a pharmaceutical dosage form in an amount effective to decrease said circulatory insufficiencies, whereby relief of rest pain or induction of healing of ulcers in said extremities occurs; the present invention provides the improvement which comprises:

administering $PGE_1$ non-intraarterially.

The terms "peripheral vascular diseases", "circulatory insufficiencies", "extremities of humans", "pharmaceutical dosage form", "rest pain", and "healing of ulcers" are used in their ordinarily accepted meanings in the art, and particularly as described in South African Patent 74/0149. However, the term "pharmaceutical dosage form" of $PGE_1$ includes the employment of either $PGE_1$, any of its known pharmaceutically acceptable salts, lower alkyl esters, or amide. See, for example, the salts and esters of $PGE_1$ described in U.S. Pat. No. 3,069,322.

The present invention describes the improvement over the prior art whereby $PGE_1$ is administered intravenously, orally, rectally, bucally, sublingually, subcutaneously, vaginally, or by other known, readily and conveniently employed non-arterial systemic routes. For example, intravenous injection is accomplished through any readily accessible human vein ordinarily employed when a substance is to be administered by the intravenous route. For example, the most convenient, and thus most preferred, injection route is through the anticubital vein (the large vein of the arm).

This intravenous route of administration has significant advantages over the previously known intraarterial method of using $PGE_1$ in peripheral vascular disease. For example, persons of limited medical training are able to easily and conveniently administer $PGE_1$ intravenously. Further, the more difficult surgical task of locating the less accessible arterial blood system and providing the drug thereto is obviated. Also the possibility of arterial injury is obviated.

For the oral route of administration, any conventional, stabilized oral formulation is employed, including capsules, compressed tablets, and the like. When oral formulations require extended stability or will endure variable or poorly controlled conditions of handling and storage, triacetin solutions of $PGE_1$ enclosed in gelatin capsules are a preferred oral formulation. See U.S. Pat. No. 3,966,962.

Additionally, the present invention shows surprising and unexpected efficacy for a route of administration which inherently requires that the $PGE_1$ pass through the lungs before transportation to the diseased extremity. Additionally, in spite of the passage of the $PGE_1$ through the lungs before transportation to the extremities, the resulting therapeutic effect is of a surprising and unexpected duration For example, the diminution or alleviation of rest pain after administration of $PGE_1$ often persists for several weeks after termination of treatment.

Further, the present administration of $PGE_1$ is effective at extremely low doses. For example, doses of $PGE_1$ are employed at which no systemic hypotensive or vasodilation effects are noted.

Accordingly, the present method proceeds at an intravenous dosage of about 1–10 μg./hr., more especially 2–4 μg./hr. and an oral dosage of 0.1 to 1.0 mg. every two hours, more especially 0.2 to 0.4 mg. every 2 hours.

$PGE_1$ is most preferably administered once per hour by intravenous injection or, more preferably infusion over about 10 to 20 min. Alternatively continuous infusion is employed.

oral dosages are administered 6–7 times per day, during the working hours. Treatment by other non-intraarterial, systemic routes of administration proceeds by a similar dosage schedule, employing dosages which maintain equivalent blood levels of $PGE_1$.

Treatment is continued for one to five days, although three days is ordinarily sufficient to assure long lasting therapeutic action. In particular, the treatment should continue until subjective (relief of rest pain) and objective (increase in peripheral skin temperature and healing of ulcers) improvement in the patient's condition is well established. In the event that systemic or side effects are observed the dosage is lowered below the threshold at which such systemic or side effects are observed.

DESCRIPTION OF THE PREFERRED EMBODIMENTS

The present invention is more particularly understood by the operation and results of the following Examples, describing the best mode for its execution. The obvious and equivalent variants of the exemplified process are, however, likewise further examples of the operation of the present invention.

EXAMPLE 1

To the following patients, suffering from peripheral vascular disease, $PGE_1$ in a saline solution is administered intravenously at a dose of 2–4 μg./hr., during a 10 min., period each hour for 3 days. No systemic or side effects are observed. The results on the affected extremities are as follows:

| Patient No. | Sex | Age Year | Ulceration | Earlier Amputation | Rest Pain | Immediate Effect on Rest Pain |
|---|---|---|---|---|---|---|
| I | Female | 81 | moderate | no | moderate | moderate improvement |
| II | Female | 68 | moderate | no | severe | complete disappearance |
| III | Female | 85 | substantial | no | slight | moderate improvement |
| IV | Female | 65 | substantial | no | severe | no effect |
| V | Female | 77 | slight | no | none | — |
| VI | Male | 71 | slight | yes | none | — |
| VII | Female | 71 | moderate | yes | severe | complete disappearance |

Following treatment the following longer-term effects are noted:

1. The severe rest pain in patients II and VII disappeared completely and did not recur for the entire period of observation, now five and one weeks, respectively.

2. With regard to ulcers, there was a deterioration in patient IV whose ulcers were initially purulent and had steadily increased since the initiation of treatment. Three other patients, who had not been considered suitable candidates for skin transplantation prior to treatment, underwent transplantation after $PGE_1$ treatment. Two such transplants were successful. Of the remaining three patients, a very definite healing has occurred in patients II and VI. The effect cannot yet be evaluated in the third patient.

EXAMPLE 2

Four patients with severe peripheral vascular disease are treated orally with $PGE_1$, as follows:

Oral administration of $PGE_1$ is commenced with two doses of 0.1 mg. per patient at one hour intervals. Thereafter 0.2 mg. of $PGE_1$ is administered every two hours. Dosing is maintained from 8:00 a.m. to 8:00 p.m. each day for two or three days, depending upon the improvement noted for the particular patient. Thereafter treatment is continued an additional three days at a dose of 0.2 mg. every four hours from 8:00 a.m. to 8:00 p.m. during the day.

The efficacy of treatment is determined by the effect on rest pain by interview, the effect on ulcer healing by visual observation, the effect on macrocirculation to the limbs, as assessed by digital pulse plethysmography and distal blood pressure, and the effect on microcirculation as measured by vital capillary microscopy. Assessments are performed before the start of treatment and after two of three days of treatment, the final assessment being made one hour prior to the last administration of drug during the day.

The treatment described above yields the following results:

Case 1: The patient is a 73 year old woman with a ten year history of ischemic ulcers of the right foot. The toes of the right foot had been amputated due to gangrene. For the six months prior to treatment, ulcers are present on the upper portion of the right foot and rest pain in the foot can be relieved only by placing the foot outside of the bed during the night. During treatment with $PGE_1$ the patient's pain is relieved during the first day of treatment. The extent of ulceration diminishes after treatment and signs of healing of the ulcers are apparent with the drying of the edges of the ulcerated tissue. One week after treatment begins, two ulcers of the lateral part of the lower leg are healed completely and the coloration of the entire foot is deemed improved. The macrocirculation and microcirculation are not changed during treatment. Mild diarrhea is observed during the first day of treatment, but no other side effects are noted.

Case 2: The patient is a 70 year old woman with a history of insulin-controlled diabetes mellitus for the past twenty-five years. Peripheral vascular disease was diagnosed three years prior to treatment and in the six months prior to treatment intense nocturnal rest pain has been experienced. Amelioration of rest pain is obtained when patient sits in bed with feet downward. The lateral part of the lower right leg exhibits a three to four centimeter ulcer and moderate edema at the time treatment is initiated. During the treatment with $PGE_1$ the rest pain subsides such that the regular analgesic therapy is not required. The ulcer begins to dry and heal and eleven days after treatment began the rest pains are completely relieved. Macrocirculation is not effected by treatment. A marked improvement is, however, noted in the microcirculation in four of five toes of each foot. During the first day, diarrhea and gastrointestinal pain are reported as side effects, but on successive days of treatment no side effects are observed.

Case 3: The patient is a 78 year old woman with a history of diabetes mellitus for the last nine years. Peripheral vascular disease was diagnosed two years prior to the commencement of treatment and eight months before treatment rest pain and ulceration of the feet is noted. Prior to the commencement of treatment, intense nocturnal rest pain is evident, requiring the patient to sit up or walk around for relief. Treatment with $PGE_1$ did not effect rest pain. However, edema decreased and the ulcers became less purulent. No side effects were noted. Macrocirculation and microcirculation are both unchanged by the treatment.

Case 4: The patient is a 65 year old man with severe peripheral vascular disease for the past five years. Three years prior to oral treatment with $PGE_1$, his left leg had been amputated and during the past year severe claudication of the right leg and nocturnal rest pain are noted. Four months prior to oral administration of $PGE_1$, intravenous administration of $PGE_1$ had resulted in a three month remission of these symptoms. On commencement of oral treatment with $PGE_1$, the nocturnal rest pain disappears and the claudication is ameliorated such that walking tolerance increased from 10 to 150 meters. No side effects are observed and macrocirculation remains unchanged during treatment. Microcirculation in the fifth toe of the right foot is improved.

I claim:

1. In the method of treating peripheral vascular disease in the extremities of humans who have circulatory insufficiencies in said extremities; which consists essentially of systemic administration to said humans of $PGE_1$ in a pharmaceutical dosage form in an amount effective to decrease said circulatory insufficiencies, whereby relief of rest pain or induction of healing of ulcers in said extremities occurs; the improvement which comprises:

administering $PGE_1$ non-intraarterially in a dosage which does not exceed
(a) about 10 μg per hour, when administered intravenously; or
(b) the dosage by any other route which is equivalent to a 10 μg per hour dose intravenously, when administered by said other route.

2. A method according to claim 1, where the extremities are the lower extremities.

3. A method according to claim 2, wherein the systemic administration is by intravenous injection.

4. A method according to claim 3, wherein the systemic administration is by intravenous infusion.

5. A method according to claim 4, wherein said pharmaceutical dosage form of $PGE_1$ comprises a pharmaceutically acceptable salt of PGE.

6. A method according to claim 4, wherein said pharmaceutical dosage form of $PGE_1$ comprises a saline solution of $PGE_1$.

7. A method according to claim 4, wherein said pharmaceutical dosage form of $PGE_1$ comprises an aqueous solution of a lower alkyl ester of $PGE_1$.

8. A method according to claim 7, wherein said lower alkyl ester of $PGE_1$ is $PGE_1$, methyl ester.

9. A method according to claim 2, wherein the systemic administration is by oral administration.

10. A method according to claim 9, wherein said pharmaceutical dosage form of $PGE_1$ comprises a pharmaceutically acceptable salt of $PGE_1$.

11. A method according to claim 9, wherein said pharmaceutical dosage form of $PGE_1$ comprises $PGE_1$, amide.

12. A method according to claim 9, wherein said pharmaceutical dosage form of $PGE_1$ comprises a lower alkyl ester of $PGE_1$.

13. A method according to claim 12, wherein said lower alkyl ester of $PGE_1$ is $PGE_1$, methyl ester.

14. A method according to claim 9, wherein said pharmaceutical dosage form of $PGE_1$ comprises a film-coated tablet containing $PGE_1$.

* * * * *

UNITED STATES PATENT OFFICE
CERTIFICATE OF CORRECTION

Patent No. 4,103,026      Dated July 25, 1978

Inventor(s) Lars A. Carlson

It is certified that error appears in the above-identified patent and that said Letters Patent are hereby corrected as shown below:

Column 6, line 33, "salt of PGE." should read -- salt of $PGE_1$. --.

Signed and Sealed this

Twenty-seventh Day of February 1979

[SEAL]

Attest:

RUTH C. MASON
*Attesting Officer*

DONALD W. BANNER
*Commissioner of Patents and Trademarks*